US007698071B2

(12) United States Patent
Harris (10) Patent No.: US 7,698,071 B2
(45) Date of Patent: *Apr. 13, 2010

(54) METHODS AND DEVICES RELATING TO ESTIMATING CLASSIFIER PERFORMANCE

(75) Inventor: Cole Coryell Harris, Albuquerque, NM (US)

(73) Assignee: Exagen Diagnostics, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/502,979

(22) Filed: Jul. 14, 2009

(65) Prior Publication Data

US 2009/0276384 A1 Nov. 5, 2009

Related U.S. Application Data

(63) Continuation of application No. 10/109,094, filed on Mar. 28, 2002, now Pat. No. 7,561,971.

(51) Int. Cl.
*G06F 19/00* (2006.01)
*G06G 7/60* (2006.01)
*G11C 17/00* (2006.01)

(52) U.S. Cl. ............................. 702/19; 703/11; 365/94
(58) Field of Classification Search ....................... None
See application file for complete search history.

(56) References Cited

U.S. PATENT DOCUMENTS

| | | | | |
|---|---|---|---|---|
| 5,909,190 | A | 6/1999 | Lo et al. ...................... | 342/159 |
| 6,182,058 | B1 | 1/2001 | Kohavi ......................... | 706/45 |
| 6,201,989 | B1 | 3/2001 | Whitehead et al. .......... | 600/476 |
| 6,238,342 | B1 | 5/2001 | Feleppa et al. .............. | 600/437 |
| 6,317,517 | B1 | 11/2001 | Lu ............................... | 382/228 |
| 6,714,925 | B1 | 3/2004 | Barnhill et al. ............... | 706/48 |
| 6,974,667 | B2 | 12/2005 | Horne et al. ................... | 435/6 |
| 7,363,165 | B2 | 4/2008 | Tusher et al. ................. | 702/19 |
| 7,561,971 | B2 | 7/2009 | Harris ......................... | 702/19 |

OTHER PUBLICATIONS

"Business intelligence—expertise," 6 pages from the CSIRO Australia website, last updated Feb. 26, 2002, http://www.cmis.csiro.au/bi/expertise.htm.
"Microarray data analysis using a genetic algorithm and K-nearest neighbor method," printed from the Microarray Data Analysis website, at http://dir.niehs.nih.gov/microarray/datamining/ on Nov. 14, 2001.
"NIPS 2000 Workshop: Unlabeled Data Supervised Learning Competition," 224 landscape-oriented pages taken from the different directories and files of http://q.cis.uoguelph.ca/~skremer/NIPS2000/, specifically top.html, menu.html, synopsis.html, rules. html, faq.html, getdata.html, data1/, data2/, data3/, data4/, submit. html, CGI/scores.cgi, finalscores.html, Workshop/index.html, Workshop/Harris/, Workshop/Aftermath/, Workshop/postmortem. html, Workshop/Introduction/, and Workshop/Results/, 2000.

Cai et al., "Supervised machine learning algorithms for classification of cancer tissue types using microarray gene expression data," 2000, printed from http://www.cpmc.columbia.edu/homepages/jic7001/cs4995/projectl.htm.
Cohn, "Active learning with a mixture of Gaussians," 1996, printed from http://www-2.cs.cmu.edu/afs/cs/project/jair/pub/volume4/cohn96a-html/node6.html.
Dietterich, "Machine learning research: four current directions," *A.I. Magazine*, 97-136, 1997.
Duin et al., "A note on core research issues for statistical pattern recognition," *Pattern Recognition Letters*, 23:493-499, 2002.
Duin, "A note on comparing classifiers," *Pattern Recognition Letters*, 17: 529-536, 1996.
Echauz and Vachtsevanos, "Radial wavelet neural networks for electroencephalographic drug detection," *Proc. 5th International Conference on Advances in Communication Control*, Jun. 26-30, 1995.
Efron, "Nonparametric estimates of standard error: the jackknife, the bootstrap and other methods," *Biometrika*, 68:589-99, 1981.
European Search Report, issued in European Application No. 03 716 892, dated Mar. 10, 2008.
Harris, "Discriminant analysis with unlabeled training data NIPS 2000 Workshop: Using Unlabeled Data for Supervised Learning," Dec. 2, 2000.
International Preliminary Examination Report, issued in Int. App. No. PCT/US2003/09657, mailed Feb. 10, 2004.
International Search Report, issued in Int. App. No. PCT/US2003/09657, mailed Oct. 8, 2003.
Lasch et al., "Imaging of human colon carcinoma thin sections by FT-IR microspectrometry," In: Mantsch and Jackson (eds.), "Infrared Spectroscopy: New Tool in Medicine," *Proceedings of SPIE*, 3257:187-198, 1998.
Lay and Hwang, "Robust construction of radial basis function networks for classification," *IEEE International Conference on* Aug. 1993, 3: 1859-1864.
Lim et al., "A comparison of prediction accuracy, complexity, and training time of thirty-three old and new classification algorithms," *Machine Learning*, 40:203-229, 2000.
Musavi et al., "Improving the performance of probabilistic neural networks," IEEE/IJCNN Joint Conference, 1:595-600, 1992.
Nabney et al., "Benchmarking beat classification algorithms," *Computers in Cardiology*, 529-532, 2001.
Notice of Allowance, issued in U.S. Appl. No. 10/109,094, mailed Mar. 10, 2009.

(Continued)

*Primary Examiner*—John S Brusca
(74) *Attorney, Agent, or Firm*—Fulbright & Jaworski L.L.P.

(57) ABSTRACT

Methods and devices, including methods and devices for estimating classifier performance such as generalization performance, are disclosed. One method includes providing multiple samples. Each sample is characterized by one or more features. This method also includes associating a feature variability with at least one of the one or more features on a feature-by-feature basis; and computing a first probability of misclassification by a first classifier using the feature variability. Devices, including integrated circuits (ICs) and field programmable gate arrays (FPGAs), that are configured for use in carrying out the present methods are also disclosed.

16 Claims, 10 Drawing Sheets

OTHER PUBLICATIONS

Office Action, issued in European Patent App. No. 03 716 892, mailed Jun. 4, 2008.

Office Action, issued in European Patent App. No. 03 716 892, mailed Sep. 24, 2009.

Office Action, issued in Japanese Patent App. No. 2003-581108, mailed Apr. 22, 2009.

Office Action, issued in U.S. Appl. No. 10/109,094, mailed Mar. 4, 2009.

Office Action, issued in U.S. Appl. No. 10/109,094, mailed Sep. 4, 2008.

Office Action, issued in U.S. Appl. No. 10/109,094, mailed Dec. 4, 2007.

Office Action, issued in U.S. Appl. No. 10/109,094, mailed Jun. 21, 2007.

Office Action, issued in U.S. Appl. No. 10/109,094, mailed Apr. 3, 2007.

Office Action, issued in U.S. Appl. No. 10/109,094, mailed Jan. 18, 2007.

office Action, issued in U.S. Appl. No. 10/109,094, mailed Jul. 14, 2006.

Office Action, issued in U.S. Appl. No. 10/109,094, mailed Apr. 19, 2005.

Office Action, issued in U.S. Appl. No. 10/109,094, mailed Jul. 29, 2004.

Office Action, issued in U.S. Appl. No. 10/109,094, mailed Apr. 8, 2004.

Ouali and King, "Cascaded multiple classifiers for secondary structure prediction," *Protein Science*, 9 (6): 1162-1176, 2000.

Poggio and Sung, "Finding human faces with a Gaussian mixture distribution-based face model," To appear in: *Recent Progress in Computer Vision*, Springer-Verlag LNCS Series, 1995.

Raudys, "Linear classifiers in perceptron design," *Proceedings of the 13th International conference on* vol. 3, Aug. 25-29, 1996, 763-767, 1996.

Response to Office Action, in European. Patent App. No. 03 716 892, dated Dec. 15, 2008.

Response to Office Action, in U.S. Appl. No. 10/109,094, dated Jan. 5, 2009.

Response to Office Action, in U.S. Appl. No. 10/109,094, dated Jun. 4, 2008.

Response to Office Action, in U.S. Appl. No. 10/109,094, dated Oct. 5, 2007.

Response to Office Action, in U.S. Appl. No. 10/109,094, dated Apr. 18, 2007.

Response to Office Action, in U.S. Appl. No. 10/109,094, dated Mar. 19, 2007.

Response to Office Action, in U.S. Appl. No. 10/109,094, dated Nov. 13, 2006.

Response to Office Action, in U.S. Appl. No. 10/109,094, dated Apr. 21, 2006.

Response to Office Action, in U.S. Appl. No. 10/109,094, dated Sep. 19, 2005.

Response to Office Action, in U.S. Appl. No. 10/109,094, dated Jan. 31, 2005.

Response to Office Action, in U.S. Appl. No. 10/109,094, dated May 3, 2004.

Singh et al., "Gene expression correlates of clinical prostate cancer behavior," *Cancer Cell*, 1:203-209, 2002.

Supplemental Response to Office Action, in U.S. Appl. No. 10/109,094, dated Feb. 26, 2009.

Tadjudin and Landgrebe, "Robust parameter estimation for mixture model," *IEEE Transactions on Geoscience and Remote Sensing*, 38(1):439-445, 2000.

Tenmoto, "Construction of classifiers," Sep. 9, 1998, 7 pages found at http://ips9.main.eng.hokudai.ac.jp/research/pattern/eng/tenmo/.

U.S. Appl. No. 60/329,322, filed Oct. 16, 2001.

METHODS AND DEVICES RELATING TO ESTIMATING CLASSIFIER PERFORMANCE

CROSS-REFERENCE(S) TO RELATED APPLICATION(S)

This is a continuation of application Ser. No. 10/109,094, filed Mar. 28, 2002, now U.S. Pat. No. 7,561,971, the entire content of which is expressly incorporated by reference.

BACKGROUND OF THE INVENTION

1. Field of the Invention

The invention relates generally to data classification. More specifically, the invention relates to estimating and evaluating classifier performance.

2. Description of Related Art

A classification algorithm, or classifier, is a method of determining the class to which a sample belongs based on a set of one or more features. A "class" is simply an attribute of the sample, which in some cases is well-defined. For example, the classes "tumor" and "normal" could be used in the design of a classifier for diagnosing whether a particular tissue sample is cancerous. Useful features for detecting cancer might include gene and/or protein expression levels measured from the tissue samples. Although the applications of classification algorithms are numerous, this diagnosis example underscores the need for accurate methods of evaluating classifier performance in certain domains.

A "sample" is any type of data. A "feature" is an aspect or characteristic of the data. For example, if the sample is a tissue, a feature of the tissue may be its protein expression level. If the sample is a credit card application, a feature of the application might be the age or income of the applicant.

For applications similar to the diagnosis example above, supervised learning techniques have been employed for the design of the classifier. Supervised learning is a kind of machine learning where the learning algorithm is provided with a set of inputs for the algorithm along with the corresponding correct outputs, and learning involves the algorithm comparing its current actual output with the correct or target outputs, so that it knows what its error is, and modify things accordingly. Such techniques are used to learn the relationship between independent features of a sample and a designated dependent attribute (i.e., the class of the sample). Most induction algorithms fall into the supervised learning category. By contrast, unsupervised learning signifies a mode of machine learning where the system is not told the "right answer"—for example, it is not trained on pairs consisting of an input and the desired output. Instead the system is given the input patterns and is left to find interesting patterns, regularities, or clusterings among them. Clustering algorithms are usually unsupervised. Supervised learning techniques utilize a training dataset in which the classes of the samples are known. Under ideal circumstances, a classifier designed to correctly classify the data in the training dataset will perform well on test data not contained in the training dataset. Such classifiers are said to generalize well. In practice, there are numerous complications that can impact the generalization performance of a classifier. Thus, simply evaluating a classifier based on training data performance alone is ill advised.

Many techniques have been developed in an effort to produce a more robust estimate of expected classifier performance. Most popular among these are crossvalidation methods. In these methods, the training dataset is partitioned into a design dataset and a test dataset. A classifier is computed from the design dataset and classifier performance is evaluated on the ability of the classifier to correctly classify the test dataset samples. The process is repeated for several distinct partitions of the training dataset, and an overall performance estimate is calculated from the collective test dataset results. The underlying principle at work is that measures of performance derived from data not included in the design process are apt to be more robust. However, it has been observed that these crossvalidation measures are not accurate in some circumstances. For example, an underlying assumption in the design of classification algorithms is that the training data accurately represents the population as a whole, i.e., that the class probability densities can be estimated from the training data. In many applications, the limited amount of data available for training renders this assumption invalid. As a result, classifiers generated based on such training data can be ineffective. "Class probability density" refers to the distribution of the class features within a particular class. For example, a single feature of a protein may have a density defined by a Gaussian with a mean of 1.232 and a standard deviation of 0.287. In more than one dimension, correlations can exist between features. These correlations are also defined by a class probability density.

SUMMARY OF THE INVENTION

Shortcomings listed above are reduced or eliminated by the present methods and devices. These methods may involve estimating performance of a classifier using one or more variabilities associated with one or more of the features characterizing the data at issue. Certain of the present methods may be characterized as supervised learning algorithms that utilize such variabilities. With the present methods, one can predict how well a classifier will perform in classifying various samples. The present methods may also be used to rank the classifiers within an ensemble (i.e., group) based upon, for example, expected performance. The present devices include field programmable gate arrays and integrated circuits, such as application specific integrated circuits, configured for use in performing the present methods. The present methods may be implemented using programs, such as computer programs, that include computer or machine readable instructions. Such programs may be translatable.

These, and other, embodiments of the present methods and devices will be better appreciated and understood when considered in conjunction with the following description and the accompanying drawings. It should be understood, however, that the following description, while indicating various embodiments of the present methods and devices, and numerous specific details thereof, is given by way of illustration and not limitation. Many substitutions, modifications, additions and/or rearrangements may be made to the embodiments discuss below within departing from the scope of the present methods and devices, and the present methods and devices include all such substitutions, modifications, additions and/or rearrangements.

BRIEF DESCRIPTION OF THE DRAWINGS

The following drawings form part of the present specification and are included to further demonstrate certain aspects of the present methods and devices. These drawings illustrate by way of example and not limitation, and they use like references to indicate similar elements.

DESCRIPTION OF ILLUSTRATIVE EMBODIMENTS

In this document (including the claims), the terms "comprise" (and any form thereof, such as "comprises" and "comprising"), "have" (and any form thereof, such as "has" and "having"), and "include" (and any form thereof, such as "includes" and "including") are open-ended transitional terms. Thus, a method or a device that "comprises," "has," or "includes" one or more elements possesses those one or more elements, but is not limited to possessing only those one or more elements. For example, a method "comprising" providing multiple samples, each sample being characterized by one or more features; associating a feature variability with at least one of the one or more features; and computing a first probability of misclassification by a first classifier using the feature variability is a method that has, but is not limited to only having, the described elements. In other words, the method possesses the listed elements, but is not excluded from possessing additional elements that are not listed. For example, the method also covers associating another feature variability with another of the one or more features. Similarly, the term "using" should be interpreted the same way. That is, for example, the phrase "using the feature variability" means using at least the feature variability.

The present methods and devices and the various features and advantageous details associated with the present methods and devices are explained more fully with reference to the nonlimiting embodiments that are illustrated in the accompanying drawings and described in the following description. Descriptions of certain well known components and processing techniques are omitted so as not to obscure the present methods and devices in unnecessary detail.

Figure 1:
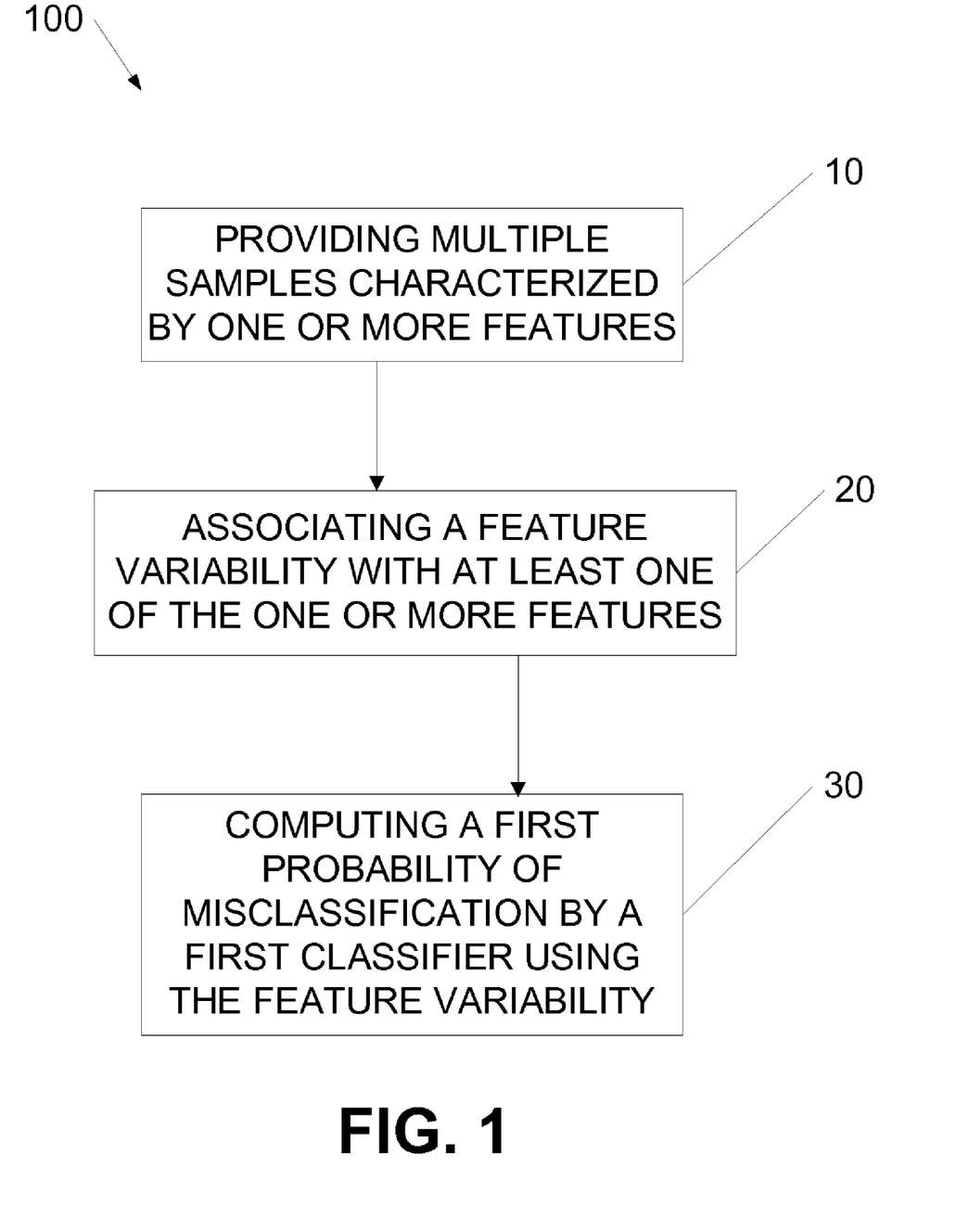
FIG. 1 is a flowchart depicting steps of one of the present methods.

FIG. 1 is a block diagram, or flow chart, depicting method 100, which is one of the present methods. As shown, method 100 includes step 10, which is providing samples, each of which is characterized by one or more features. In those instances in which the class or classes of the samples are known, the samples may be thought of as a training dataset, or as training data. By way of example, these samples might be tissue samples and the one or more features may include gene and/or protein expression levels. Such gene and/or protein expression levels may be measured within diseased regions of tissues or in extracellular bodily fluids (such as serum or urine). Other tissue features may include extracellular components such as small organic molecules; cellular features such as attributes derived from cell nuclei images, including, for example, radius, symmetry, and texture; and features at the tissue level including, for example, density and orientation of cells.

Step 20 of method 100 is associating a feature variability with at least one of the features. "Associating" a feature variability with a feature involves any manner of linking, or connecting, a variability with a feature. Thus, estimating a feature variability of at least one of the features is a way of "associating" a feature variability with at least one of the features. "Associating" a feature variability with a feature may also be described as attributing a feature variability to a feature. Consistent with step 20, the same feature variability may be associated with different features, or a different feature variability may be associated with different feature.

In another embodiment, step 20 may involve associating a feature variability with at least one of the features on a feature-by-feature basis. Associating a feature variability with at least one feature "on a feature-by-feature basis" means that a feature variability is associated with a feature based on a decision tailored to that particular feature. Subsequently, another feature variability, which may or may not be different from the first feature variability, may be associated with another feature in the same fashion.

A "feature variability" is a value that represents the potential range into which the value of the feature may fall. A feature variability associated with a particular feature may be obtained through repeated measurements of the feature, and may be expressed in terms of a frequency. For example, a feature frequency, and thus a feature variability, could be expressed as 50 kilo Hertz (kHz)+/−50 Hertz (Hz). As an alternative to additive variabilities, multiplicative variabilities—such as 50 kHz*(100%+/−0.1%)—may also be used with any of the present methods. Whatever feature variabilities are associated may be assumed to hold, or be consistent, for the remainder of the method. This is true for all of the present methods.

When it is difficult to obtain a large number of measurements on which to base a feature variability association, such as an estimate, as is sometimes the case when the one or more features comprise gene or protein expressions in biological samples, conservative estimates of feature variability may be used.

Continuing with both versions of step 20, as an alternative to estimating a feature variability based on the use of one or more measurements, a feature variability that is simply stated from experience with the particular type of sample may be associated with a feature. For example, if a particular feature typically has a measurement error on the order of twenty percent of the measured value of the feature, a feature variability that uses the twenty percent error value may be associated with the feature. This twenty percent error value may be thought of as an estimate. Such an estimate or estimates may vary from feature to feature. For example, in cases where measurements of a particular feature possess a low signal-to-noise ratio, an estimate of the variability for this feature will be larger than for a feature with a higher signal-to-noise ratio.

Continuing with FIG. 1, step 30 involves computing a first probability of misclassification by a first classifier using the feature variability (from step 20). The first classifier, may be computed using a subset of the samples provided during step 10. Such a subset of samples may be characterized as a design subset of samples, or as having design samples. The classifier may be any classification algorithm that generates sample scores as described by the following pseudocode:

```
If(f_j(x) > limit(j))
    sample is member of class j
else
    sample is not member of class j,
``` where $f_j(x)$ is a scoring function, j denotes a particular class, and x is a vector of features for the input sample. Suitable classifiers include, but are not limited to, linear and quadratic discriminant function classifiers, neural network classifiers, K-Means classifiers, support vector machines (SVMs), and Mahalanobis distance classifiers. "Computing" means establishing or ascertaining, such as by calculating; thus, "computing" is not limited to an action requiring the use of a computer or machine.

In the prior art known as kernel methods, kernel density estimates have been used to model class probability densities. In these methods, a Gaussian or other kernel function is associated with each sample within the class, and the class probability density is modeled as a sum over these functions. The parameters defining the Gaussian or other function are selected with the aim of deriving a smooth probability density. Smoothness in this context means that there are no large variations in the density between samples. Thus, the parameters defining the kernel function will depend on the number of samples and the spacing of samples within a class. These probability density estimates are subsequently used to design a classifier.

By contrast, in the present methods, a feature variability is associated with at least one or more features without regard to the smoothness of the probability density, and the feature variability is used in computing a probability of misclassification for an existing classifier.

Figure 2:
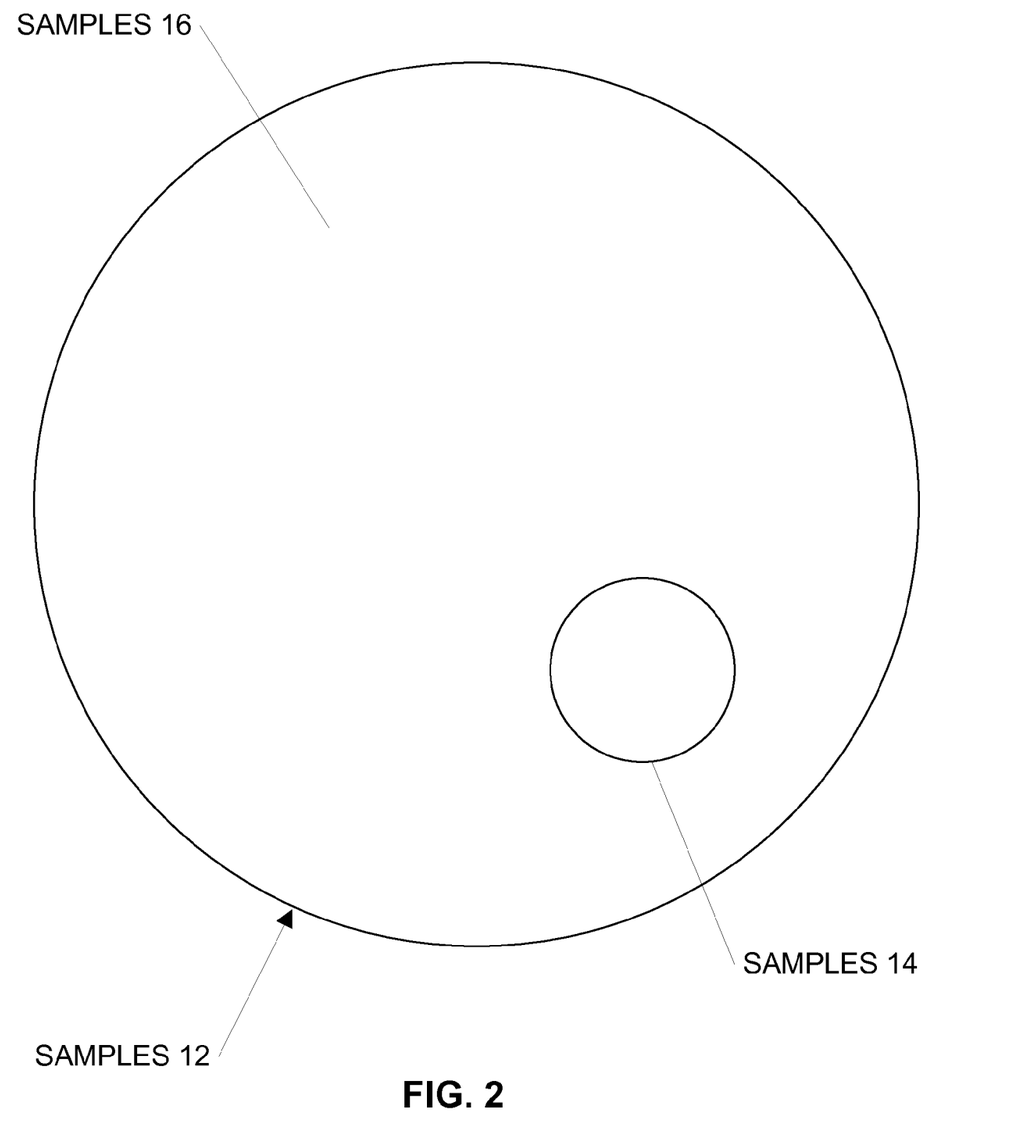
FIG. 2 depicts one arrangement of design and test subsets of samples that may be used consistently with the present methods.
Figure 3:
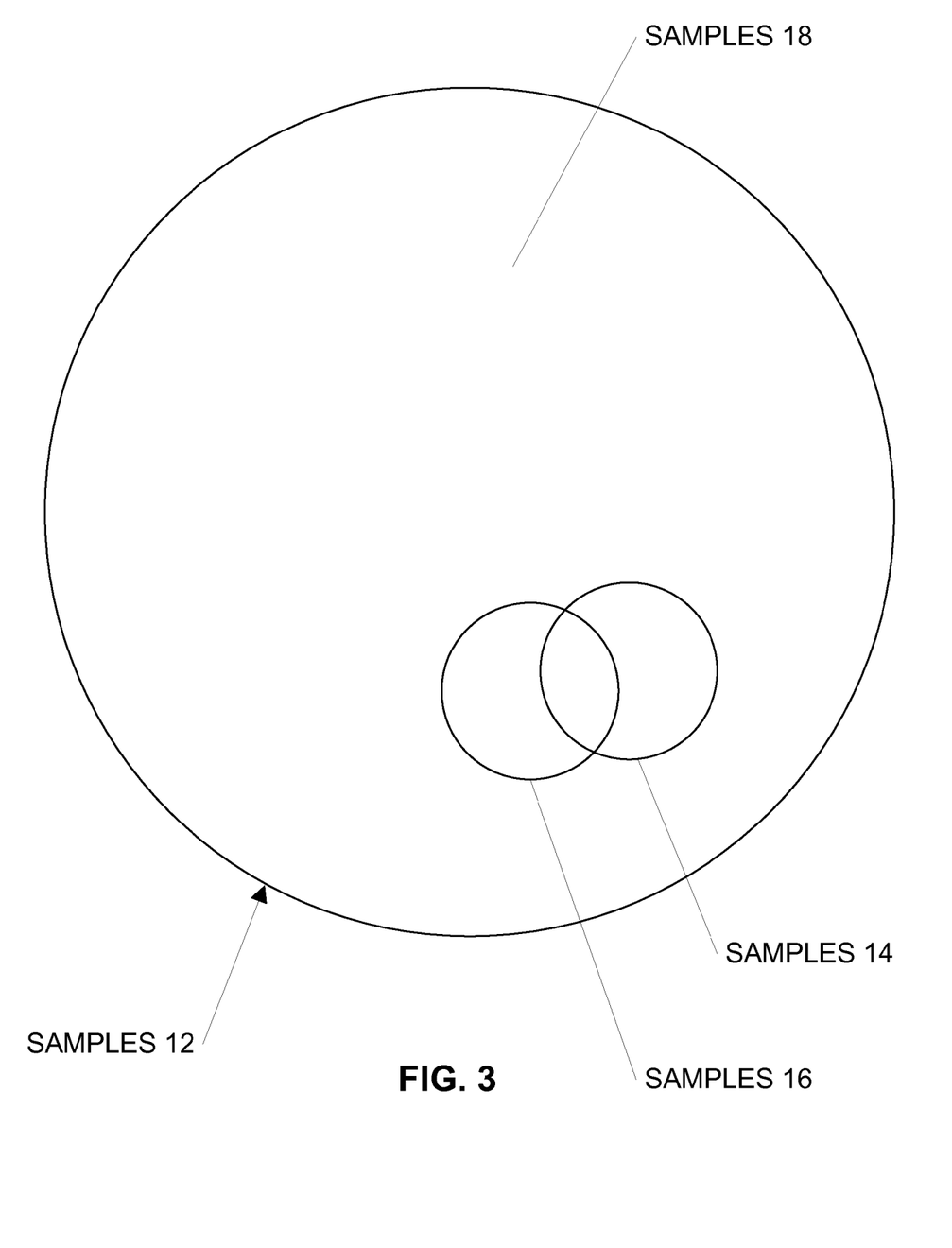
FIG. 3 depicts another arrangement of design and test subsets of samples that may be used consistently with the present methods.
Figure 4:
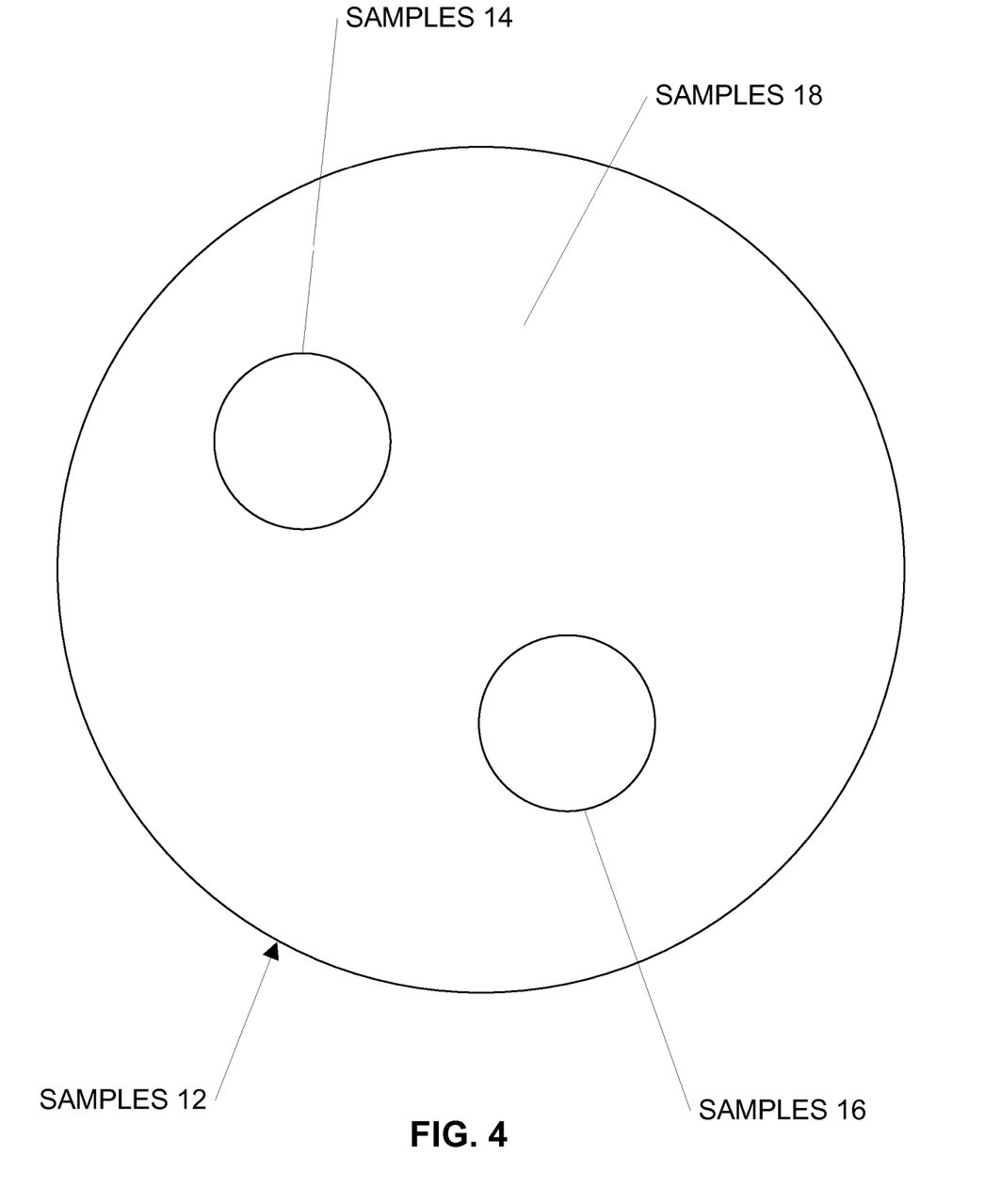
FIG. 4 depicts yet another arrangement of design and test subsets of samples that may be used consistently with the present methods.

One manner of achieving the computing of step 30 includes computing scores for each of the samples in a second subset of samples taken from the samples provided in step 10. Such a second subset of samples may be characterized as a test subset of samples, or as having test samples. The first classifier, which may be computed using a subset (which may be characterized as a design subset) of the samples provided in step 10, may then be evaluated by using it to score a sample or samples, which may be thought of as a test subset of samples, taken from the samples provided in step 10. FIGS. 2-4 illustrate different arrangements of design and test subsets of samples that may be used consistently with the present methods.

FIG. 2 shows samples 12, which represent the samples provided in step 10. FIG. 2 also shows samples 14, which represent design samples taken from samples 12. The first classifier referenced above may be computed using, for example, samples 14. FIG. 2 also shows samples 16, which represent the samples in samples 12 other than samples 14. Samples 16 may be characterized as test samples. One manner of achieving the computing of step 30 includes computing scores for each of the samples in samples 16. FIG. 2 illustrates that samples 16 and samples 14 are exclusive and, thus, do not overlap. One version of the arrangement of samples shown in FIG. 2 involves using all but one of samples 12 for the design samples (i.e., samples 14) used in computing the first classifier, and testing the first classifier by scoring the one remaining test sample (i.e., samples 16). This version is known as "leave one out cross-validation." In another embodiment, at least one of the samples in samples 16 is also one of the samples in samples 14. This overlap is illustrated in FIG. 3. FIG. 3 shows another alternative to the situation depicted in FIG. 2—samples 18, which are those samples in samples 12 other than samples 14 and 16. Although referred to as samples (plural) 12, 14, 16, and 18, only one sample may be contained in any of samples 12, 14, 16, and 18. Another alternative to the situation depicted in FIG. 3 is depicted in FIG. 4, and involves the design samples (i.e., samples 14) and the test samples (i.e., samples 16) being distinct and non-overlapping and not making up the entirety of samples 12—that is, samples 18 exist, too.

Continuing with an explanation of computing scores for each of the test samples, one manner of computing a score involves the use of a linear discriminant classifier for scoring samples. Thus, the first classifier described above may be a linear discriminant classifier. In such an embodiment, a hyperplane may be determined that best separates a known and an unknown (such as an estimate). In such an embodiment, a score for a particular sample is the Euclidean distance from that hyperplane.

Continuing with the one manner of achieving the computing of step 30 identified above, this manner also includes estimating the variability of the score or scores (i.e., the score variability) using a locally linear approximation of $f_j(x)$ in the neighborhood of a sample vector as follows:

$$f_j(x+dx) \approx a \cdot dx + b \quad (1)$$

where a is the gradient of $f_j$ at x, and b is the value of $f_j$ at x. Using this linear approximation of $f_j$, the variance of $f_j$ can be computed from the equation:

$$\sigma^2(f_j(x)) = \Sigma a_i^2 * \sigma_i^2 \quad (2)$$

where $a_i$ is the $i^{th}$ component of the gradient in equation (1), and $\sigma_i^2$ is the feature variability of the $i^{th}$ feature (this feature variability may be obtained as outlined in step 20 above). Continuing, this manner of computing a first probability of misclassification of the first classifier using the feature variability (which first probability may reflect how well a classifier will perform or, in other words, how well a classifier generalizes) includes computing a first probability of misclassification of the first classifier for the design samples used in computing the first classifier. For example, given the score(s) and the score variability(ies) for the test samples, one may compute a first probability of misclassification of the first classifier for the design subset via a Gaussian mixture model of the score distributions for each class as follows (using the example of a linear discriminant function classifier):

$$\text{class } j \text{ score distribution} = \rho(\text{score}) \quad (3)$$

$$= \frac{1}{N} \sum_{i=1}^{N} \frac{1}{\sqrt{2\Pi\sigma_i^2}} e^{\frac{-(\text{score}-\text{score}_i)^2}{2\sigma_i^2}}$$

where score is the Euclidean distance from the hyperplane (as explained above), $\text{score}_i$ is the score for the $i^{th}$ sample, N is the number of samples in class j, and $\sigma_i^2$ is the score variability for sample l. Those of skill in the art will understand that score will vary depending on the type of classifier being computed. For example, for a neural network classifier, score would be a complex function. From equation (3), the probability of misclassification for a particular class j is given by:

$$\text{Probability of misclassification for class } j = \int_{\text{limit}}^{\infty} \rho(\text{score}) d(\text{score}) \quad (4)$$

where the limit is given by the classifier design. Continuing with this manner, the misclassification probability for a given design subset is given by the sum over classes:

$$\text{Probability of misclassification for design subset} = \sum_j \pi_j * \begin{pmatrix} \text{Probability of misclassification} \\ \text{for design subset and class } j \end{pmatrix}. \quad (5)$$

where $\pi_j$ is the a priori probability of class j.

Figure 5:
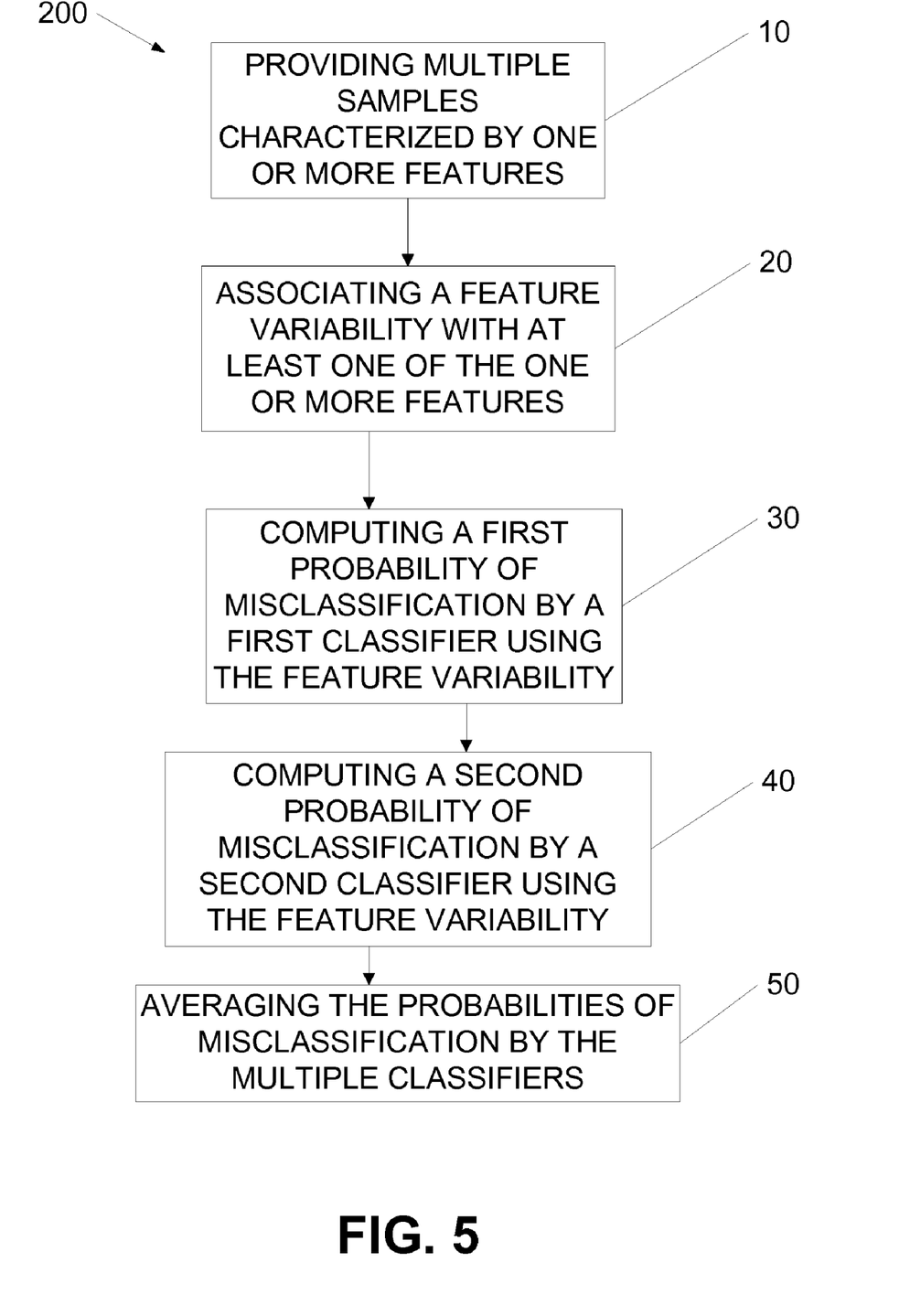
FIGS. 5-9 are flowcharts depicting steps of different versions of the present methods.

FIG. 5 illustrates another of the present methods, which is an extension of method 100. As shown in FIG. 5, method 200 includes steps 10, 20, and 30 of FIG. 1, and further includes step 40, which is computing a second probability of misclassification by a second classifier using the feature variability (from step 20). Step 40 may be achieved using the manner of achieving step 30 set forth above. In performing the steps of method 200, the first probability of misclassification may be computed for a first design subset, the first probability may be stored in a computer readable medium, and the second probability of misclassification may be computed for another design subset. In this way, a probability of misclassification for each design subset within the samples provided in step 10 (i.e., the training dataset) may be calculated. Alternatively, less than all such probabilities may be calculated in accordance with method 200. Step 50 of method 200 is averaging the probabilities of misclassification by the multiple classifiers that have been computed. The average may serve as an estimate of the performance of a final classifier.

Figure 6:
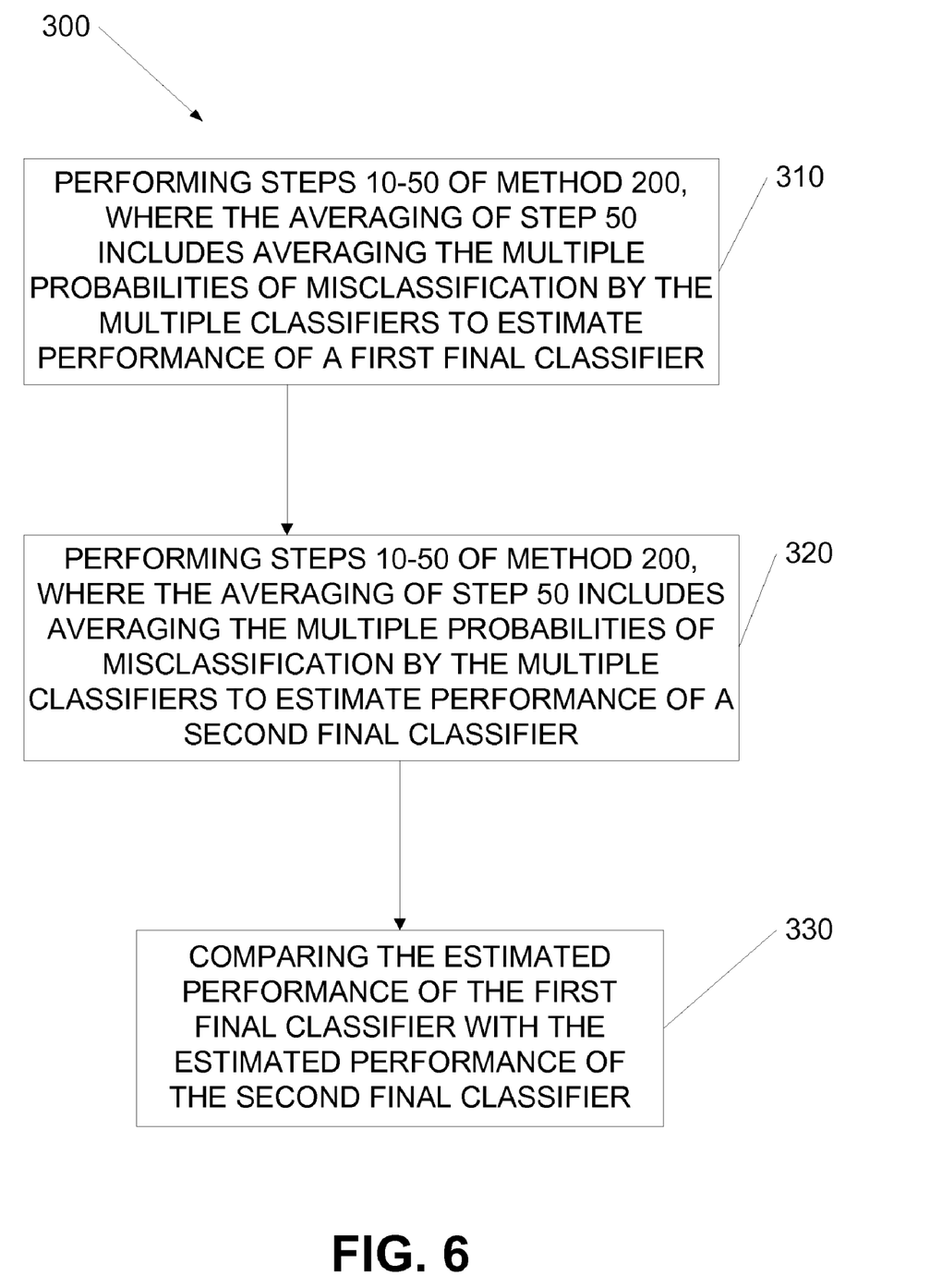

FIG. 6 illustrates another of the present methods. Method 300 is a method of comparing two or more classifiers, and is suited to ranking an ensemble of classifiers. Method 300 may also be characterized as a method useful for comparing the estimated performance of two or more classifiers. As shown in FIG. 6, method 300 includes step 310, which is performing steps 10-50 (i.e., steps 10, 20, 30, 40, and 50) of method 200, where the averaging of step 50 includes averaging the multiple probabilities of misclassification by the multiple classifiers to estimate performance of a first final classifier. Step 320 of method 300 is performing steps 10-50 of method 200, where the averaging of step 50 includes averaging the multiple probabilities of misclassification by the multiple classifiers to estimate performance of a second final classifier. Method 300 also includes step 330, which is comparing the estimated performance of the first final classifier with the estimated performance of the second final classifier. In this way, method 300 is suited to determining which classifier among a group of two or more classifiers will generalize the best.

When performing step 310 of method 300, the feature variability or variabilities of features may be different than the feature variability or variabilities used in performing step 320 of method 300. For example, in performing method 300, the samples used may be a car part. The car parts may each be characterized by multiple features, including the part's acoustic resonance spectra, dimensions, and material properties. In performing step 310, the performance of step 20 may involve associating a feature variability with 3 features. The choice of which 3 features will impact the estimated performance of the first final classifier. In performing step 320, the performance of step 20 may involve associating a feature variability with 2 features that are different than the 3 features chosen in connection with step 310. The choice of which 2 features to use in performing step 20 will impact the estimated performance of the second final classifier. Altering the features chosen for use in performing steps 310 and 320 allows the user the ability to ultimately choose which classifier has the best ability to generalize.

Further, there are many different ways to generate subsets of one or more features for use in performing the steps of the present methods. For example, different feature subsets may be generated using any suitable algorithm. One such example is described below.

Figure 7:
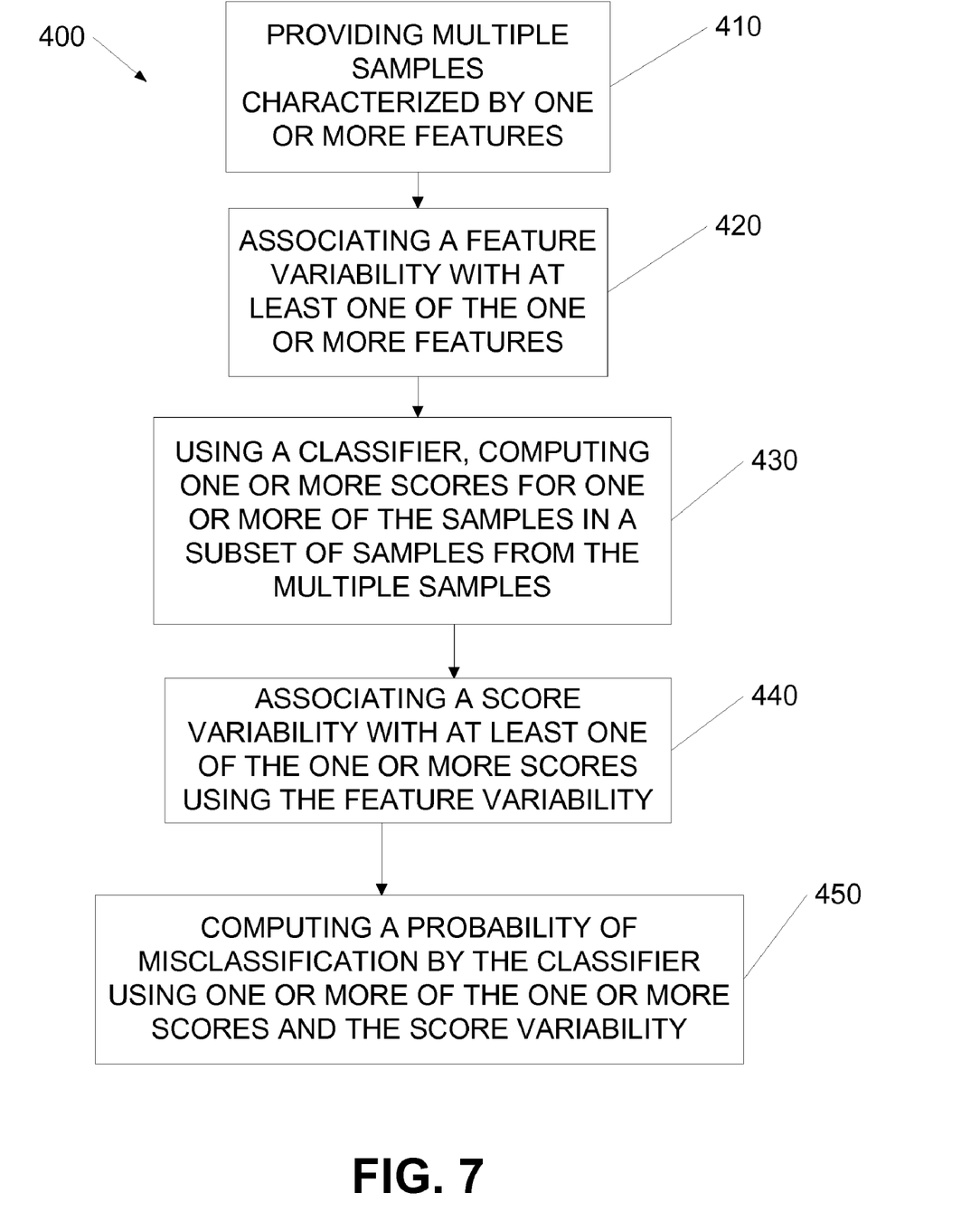

FIG. 7 illustrates another of the present methods. Method 400 includes step 410, which is providing multiple samples, each of which is characterized by one or more features. The discussion above with respect to step 10 of method 100 applies equally to step 410.

Step 420 of method 400 involves associating a feature variability with at least one of the features. The discussion above with respect to step 20 of method 100 applies equally to step 420.

Continuing with FIG. 7, step 430 involves computing one or more scores for one or more samples in a subset of samples from the multiple samples using a classifier. Such a subset of samples may be characterized as a design subset of samples, or as having design samples. (The use of design and test subsets of samples with method 400 is the same as the use of design and test samples outlined above in the description referring to FIGS. 2-4.) The classifier may be any classification algorithm that generates sample scores as described using the pseudocode above. Suitable classifiers include, but are not limited to, those classifiers listed above.

Continuing with FIG. 7, step 440 of method 400 involves associating a score variability with at least one of the one or more scores using the feature variability from 420. One manner of achieving this associating includes estimating the variability of the score or scores (i.e., the score variability) using a locally linear approximation of $f_j(x)$ in the neighborhood of the sample vector using equation (1). Using this linear approximation of $f_j$, the variance of $f_j$ can be computed using equation (2).

Continuing with FIG. 7 and method 400, step 450 involves computing a probability of misclassification by the classifier using one or more of the one or more scores and the score variability. One manner of computing this probability for a given subset includes the use of a Gaussian mixture model of the score distributions for each class using equation (3). From equation (3), the estimated probability of misclassification for a particular class j is given by equation (4). Continuing with this manner, the misclassification probability for a particular design subset is given by the sum over classes according to equation (5).

Figure 8:
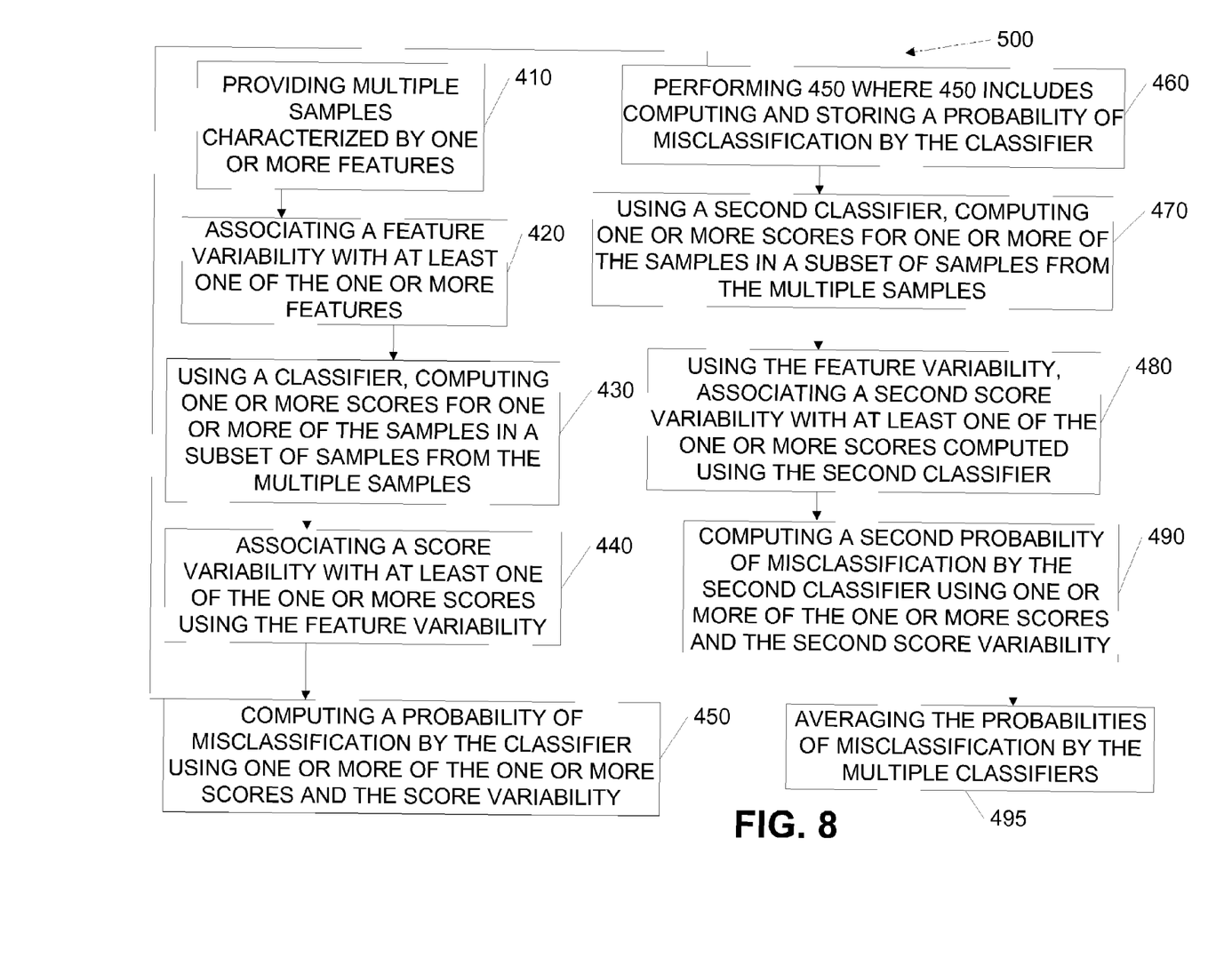

FIG. 8 illustrates another of the present methods, which is an extension of method 400. As shown in FIG. 8, method 500 includes steps 410-450 of method 400, and further includes step 460, which refines step 450 to computing and storing a probability of misclassification by the classifier using one or more of the one or more scores and the score variability. The probability may be stored, for example, in a computer readable medium, such as memory.

Continuing with method 500, step 470 involves computing one or more scores for one or more samples in a subset of samples from the multiple samples using a second classifier. Step 470 may be carried in the same way or ways step 430 may be carried out. Step 480 involves, using the feature variability, associating a second score variability with at least one of the one or more scores computed using the second classifier. Step 480 may be carried in the same way or ways step 440 may be carried out. Step 490 involves computing a second probability of misclassification by the second classifier using one or more of the one or more scores computed using the second classifier and the second score variability. Step 490 may be carried in the same way or ways step 450 may be carried out.

In performing the steps of method 500, the (first) probability of misclassification may be computed for a first design subset, the first probability may be stored in a computer readable medium, and the second probability of misclassification may be computed for another design subset. In this way, a probability of misclassification for each design subset within the samples provided in step 410 (i.e., the training dataset) may be calculated. Alternatively, less than all such probabilities may be calculated in accordance with method 500. Step 495 is averaging the probabilities of misclassification by the multiple classifiers that have been computed. The average may serve as an estimate of the performance of a final classifier.

Figure 9:
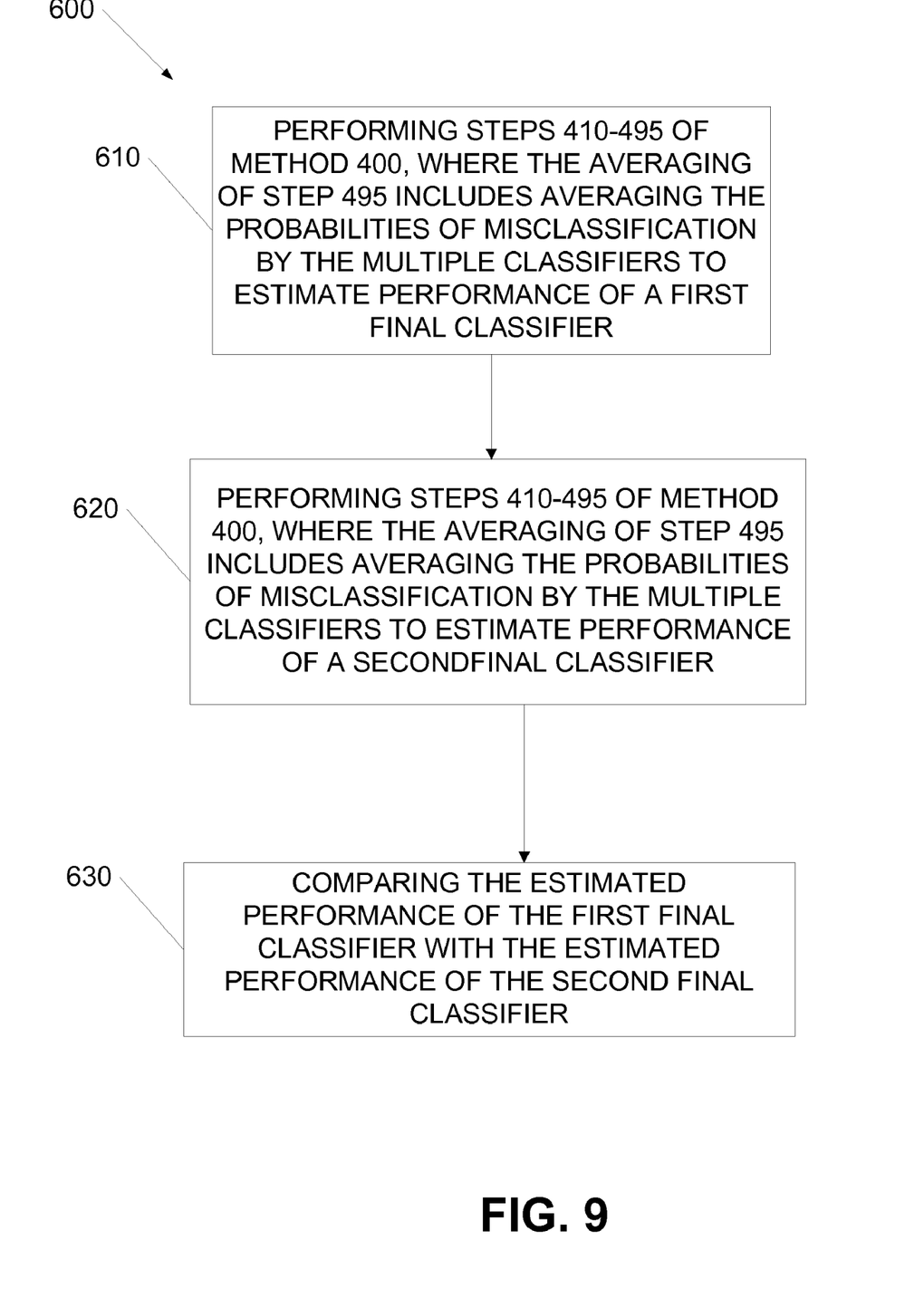

FIG. 9 illustrates another of the present methods. Method 600 is a method of comparing two or more classifiers, and is suited to ranking an ensemble of classifiers. Method 600 may also be characterized as a method useful for comparing the estimated performance of two or more classifiers. As shown in FIG. 6, method 600 includes step 610, which is performing steps 410-495 of method 500, where the averaging of step 495 includes averaging the multiple probabilities of misclassification by the multiple classifiers to estimate performance of a first final classifier. Step 620 of method 600 is performing steps 410-495 of method 500, where the averaging of step 495 includes averaging the multiple probabilities of misclassification by the multiple classifiers to estimate performance of a second final classifier. Method 600 also includes step 630, which is comparing the estimated performance of the first final classifier with the estimated performance of the second final classifier. In this way, method 600 is suited to determining which classifier among a group of two or more classifiers will generalize the best.

When performing step 610 of method 600, the feature variability or variabilities of features may be different than the feature variability or variabilities used in performing step 620 of method 600. The discussion above concerning the performance of steps 310 and 320 of method 300 applies equally to the performance of steps 610 and 620 of method 600.

Sample Applications

The present methods are suited for more accurately estimating the performance of classifiers suited, for example, for use in all applications addressed by pattern recognition technology. The present methods enable improved estimations of the likely "real world" performance of a classifier than what were previously available, regardless of the application involved. For example, the present methods enable more accurate assessments of the likely performance of classifiers in the following applications: medical diagnoses; financial market prediction; reviewing parts for different systems such as cars, or the like; credit card applications; credit card fraud detection; retail transactions; insurance applications; fraud detection on any application; nondestructive evaluation of parts, utilizing the parts' acoustic resonance spectra; and personal identification, to name a few.

As will be understood by those having skill in the art with the benefit of this disclosure, the present methods and the techniques for carrying them out may be implemented in any number of various media or devices. For example, any of the present methods may be embodied by one or more programs. Those programs may include machine-readable instructions for implementing any of the present methods, and may be stored in any of a number of machine-readable media including, but not limited to, a CD-ROM, a floppy disk, a hard disk drive, a server, a memory card, RAM, or the like. In another embodiment, any of the present methods may be embodied in an integrated circuit, such as application specific integrated circuit (ASIC), or in a field programmable gate array (FPGA). In another embodiment, any of the present methods may be embodied by a combination of hardware and software; for instance, certain instructions may be executed by a chip running appropriate firmware. In another embodiment, any of the present methods may be embodied by a kit, such as a software developer's kit. Such a kit may include not only software, but also any corresponding hardware to execute the software. For instance, a kit may include a computer board along with drivers and software to be run by that board. Those having skill in the art will recognize that the methods of this disclosure may be implemented by other means known in the art to achieve an identical or similar result. All such means are considered to be within the scope of the present methods.

The following examples are included to demonstrate specific embodiments of the present methods. It should be appreciated by those of skill in the art that the techniques disclosed in the examples that follow represent techniques discovered by the inventor to function well in the practice of these methods, and thus can be considered to constitute specific modes for their practice. However, those of skill in the art should, in light of this disclosure, appreciate that many changes can be made in the specific embodiments that are disclosed, and still obtain a like or similar result without departing from the scope of the present methods.

Example 1

To evaluate the accuracy of the present methods at estimating classifier performance (e.g., the probabilities of misclassification discussed above), one of the present methods was tested on multiples classifiers exhibiting a wide range of classification accuracy.

To start, a synthetic dataset was developed. This dataset included 212 samples, each sample characterized by one or more features. The 212 samples were equally split between two classes. 100 total features were included. Of the 100 features, two correlated with the class label, and thus were useful for classification. The remaining 98 features contained only noise. A feature variability of 10% was associated with all features. Twenty samples were randomly selected from the synthetic dataset to serve as a training dataset from which design and test subsets could be generated. The balance of the data—192 samples—were reserved for use as a validation dataset.

A feature selection technique employing a genetic algorithm was used to generate the ensemble of classifiers. For a large population of classifiers relative to the number of possible accurate classifiers, only a portion of the classifiers built from the population feature subsets can be accurate. Thus, the remaining classifiers must be less accurate. This fact was considered, and the genetic algorithm feature selection technique was applied with a small specified size of feature subset (three features) and a large specified initial population of total feature subsets (1000). A linear discriminant classifier was designed from each subset of features, and the performance of the classifier was evaluated. Next, new feature subsets were generated by preferentially selecting features used in the more accurate classifiers among those tested. This process was iterated until no more accurate classifiers were found with subsequent iterations. This last step may be described as convergence. Note that for the synthetic data employed in this example, there were relatively few highly accurate possible classifiers (as evidenced by FIG. 10, discussed in more detail below), namely those that used both of the features that were correlated with the class label. A larger number of mediocre classifiers may be designed using one of the two correlated features. Inaccurate classifiers may be designed by utilizing only uncorrelated features.

Figure 10:
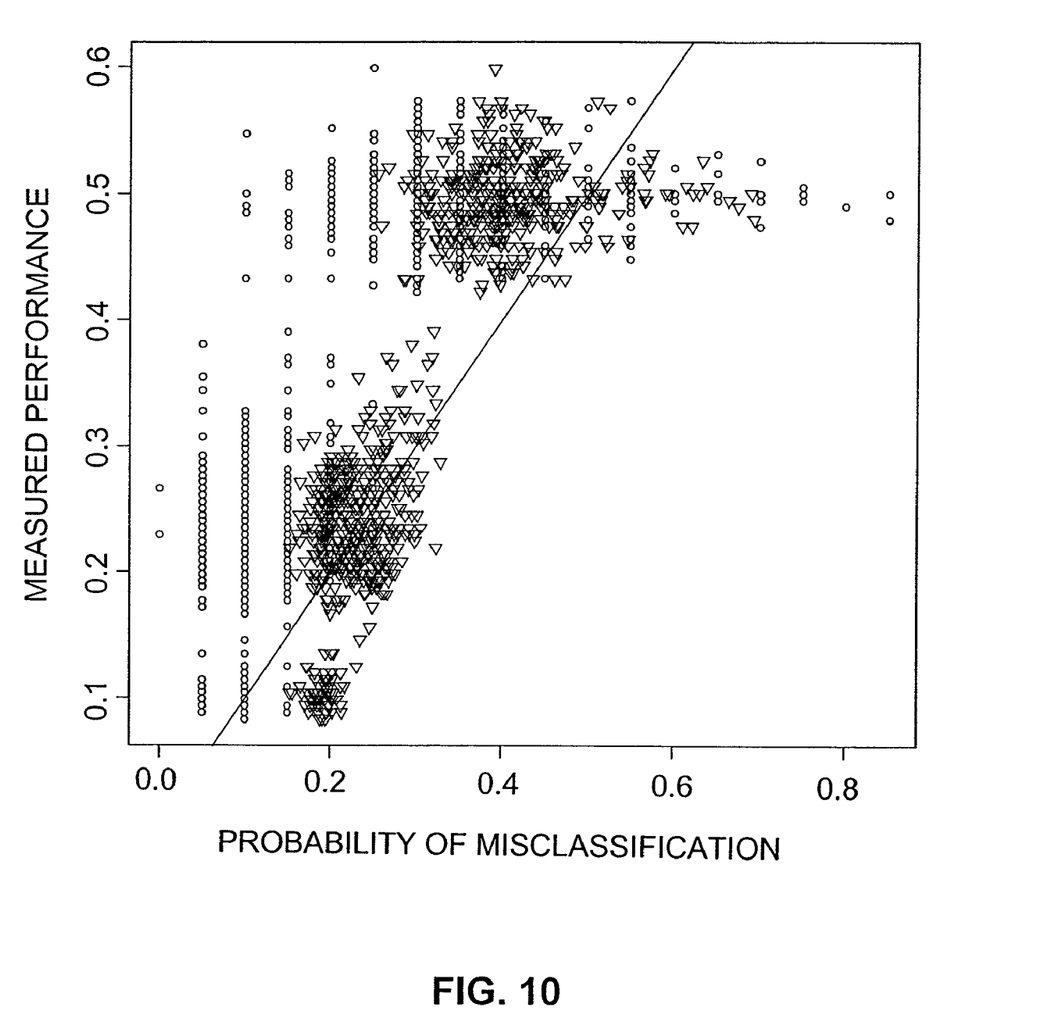
FIG. 10 depicts the results of comparing estimates of classifier performance computed using one version of the present methods with estimates of classifier performance generated using an old method.

After convergence, classifiers designed from the population feature subsets exhibited the desired wide range of accuracies. Next, a probability of misclassification was computed in accordance with method 100 for each of these classifiers, using only the training dataset of twenty randomly selected samples. Next, the generalization performance of each classifier was tested on samples from the validation dataset. FIG. 10 depicts the results of this exercise.

In FIG. 10, the horizontal axis denotes the probability of misclassification for the classifiers being tested. The vertical axis denotes the measured performance for the classifiers being tested. The solid line signifies a perfect solution—i.e., measured performance equals predicted performance. The circles denote the probabilities of misclassification computed for 861 classifiers based on the measure routinely applied prior to the present methods: the number of crossvalidation errors. The upside-down triangles in FIG. 10 are probabilities of misclassification for the same 861 classifiers computed as described above (i.e., through the convergence procedure).

The version of the present methods used resulted in a set of predictions displaying less scatter about the solid line than the routinely applied measure. This observation can be quantified in two measures: the rms error and the correlation coefficient. The rms error is a measure of the absolute error over the ensemble, or group, of classifiers. However, in applications where only ranking classifier performance is required, the absolute accuracy of the estimate is secondary to the ability to compare the performance of two or more classifiers. In such a case, the correlation coefficient—which is the correlation between, or ratio of, the predicted performance and measured performance—is a better indicator.

TABLE 1

| measures of performance | prior crossvalidation method | one version of the present methods |
|---|---|---|
| rms error | .164 | .088 |
| correlation coefficient | .749 | .839 |

As the results in Table 1 illustrate, the version of the present methods that was used provides estimates of performance that are significantly more accurate than the estimates generated by a widely-used alternative.

Example 2

Shown below is S source code that is suitable for carrying out steps described herein, and particularly steps to be performed in conjunction with method 100. This source code is exemplary only and does not limit the scope of the claims. It simply represents one specific embodiment for carrying out steps associated with the present methods and is included for the convenience of the reader in this regard. Those of skill in the art having the benefit of this disclosure will recognize that a wide variety of computational techniques and/or different types of corresponding source code may be used in implementing the present methods. The references to Eq's 1-5 in the code below are references to equations (1)-(5) above.

```
classifierscore<-function(data,cl,variability){
    # demonstration of classifier performance estimation
    # for binary diagonal qda classifier,
    # apriori probabilities assummed equal to sample proportions
    # leave-one-out crossvalidation
```
```
    # inputs
    # data - n row X m column matrix
    #     n samples
    #     m features
    # cl - vector of length n samples
    #     ith element denotes class of ith sample
    # variability - vector of length m features
    #     ith element denotes variability of ith feature
    numberofsamples<-length(cl)
    numberofclass0<-length(which(cl==0))
    numberofclass1<-length(which(cl==1))
    probmisclass0<-0
    probmisclass1<-0
    #loop over design subsets of samples
    for(i in 1:numberofsamples){
        # remove one sample from training for testing
        data2<-data[-i,]
        cl2<-cl[-i]
        meanclass0<-mean(data2[cl2==0,])
        meanclass1<-mean(data2[cl2==1,])
        stddevclass0<-apply(data2[cl2==0,],2,var)^.5
        stddevclass1<-apply(data2[cl2==1,],2,var)^.5
        distfromclass0<-sum(((data[i,]-meanclass0)/
    stddevclass0)^2)^.5
        distfromclass1<-sum(((data[i,]-meanclass1)/
    stddevclass1)^2)^.5
        # sample score
        score<-distfromclass0-distfromclass1
    # gradient calculation (Eq 1)
        gradientofscore<-(1/distfromclass0)*(1/stddevclass0^2)-
    (1/distfromclass1)*(1/stddevclass1^2)
        # variance calculation (Eq 2)
        varianceofscore<-sum((gradientofscore^2)*(variability^2))
    # Eq's 3,4
        if(cl[i]==0){
            probmisclass0<-probmisclass0+(1.-
    pnorm(0,score,varianceofscore^.5))/numberofclass0}
        else{
            probmisclass1<-
    probmisclass1+pnorm(0,score,varianceofscore^.5)/numberofclass1}
    }
    # Eq 5
    probmisclassification<-
    (numberofclass0*probmisclass0+numberofclass1*probmisclass1)/
    (numberofclass0+numberofclass1)
    classifierscore<-1.-probmisclassification
    # estimate of classifier performance
    return(classifierscore)
                }
```

I claim:

1. A computer-implemented method for estimating performance of a classifier comprising:

using suitably programmed hardware to associate a feature variability with at least one of one or more features that characterize a sample from multiple samples, each of which is characterized by one or more features;

using the classifier to compute, with the hardware, one or more scores for one or more samples in a subset of samples from the multiple samples, where the classifier can be used to determine a class to which a sample belongs based on the one or more features that characterize that sample;

using the hardware to associate a score variability with at least one of the one or more scores using the feature variability; and computing, with the hardware, a probability of misclassification by the classifier using one or more of the one or more scores and the score variability.

2. The computer-implemented method of claim 1, where the multiple samples are multiple tissue samples.

3. The computer-implemented method of claim 1, where the classifier is a linear discriminant function classifier.

4. The computer-implemented method of claim 1, where the classifier is a quadratic discriminant function classifier.

5. The computer-implemented method of claim 1, where the classifier is a neural network classifier.

6. The computer-implemented method of claim 1, where the feature variability is estimated using multiple measurements of one of the one or more features.

7. The computer-implemented method of claim 1, where the using hardware to associate a score variability with at least one of the one or more scores includes using a linear approximation of the classifier.

8. A physical computer readable medium comprising machine-readable instructions for implementing the computer-implemented method of claim 1.

9. A computer-implemented method comprising:
   using suitably programmed hardware to associate a feature variability with at least one of one or more features on a feature-by-feature basis, the one or more features characterizing a sample from multiple samples, each of which is characterized by one or more features;
   computing, with the hardware, a first probability of misclassification by a neural network classifier using the feature variability; and
   computing, with the hardware, a first probability of misclassification by a classifier using the feature variability, where the classifier can be used to determine a class to which a sample belongs based on the one or more features that characterize that sample.

10. The computer-implemented method of claim 9, where the multiple samples are multiple tissue samples.

11. The computer-implemented method of claim 9, where the feature variability is estimated using multiple measurements of one of the one or more features.

12. A computer-implemented method comprising:
   using suitably programmed hardware to associate a feature variability with at least one of one or more features on a feature-by-feature basis, the one or more features characterizing a sample from multiple samples, each of which is characterized by one or more features; and
   computing, with the hardware, a first probability of misclassification by a first classifier using the feature variability, where the first classifier can be used to determine a class to which a sample belongs based on the one or more features that characterize that sample;
   where the computing, with the hardware, a first probability of misclassification by a first classifier includes using a linear approximation of the first classifier prior to compute the first probability of misclassification.

13. A physical computer readable medium comprising machine-readable instructions for implementing the computer-implemented method of any of claims 9, 10, 11, and 12.

14. A computer-implemented method for estimating performance of a classifier comprising:
   using suitably programmed hardware to associate a feature variability with at least one of one or more features that characterize a sample from multiple samples, each of which is characterized by one or more features;
   using a first classifier to compute, with the hardware, one or more first scores for one or more first samples in a subset of samples from the multiple samples, where the first classifier can be used to determine a class to which a sample belongs based on the one or more features that characterize that sample;
   using the hardware to associate a first score variability with at least one of the one or more first scores using the feature variability;
   computing, with the hardware, a first probability of misclassification by the first classifier using one or more of the one or more first scores and the first score variability;
   using a second classifier to compute, with the hardware, one or more second scores for one or more second samples in a subset of samples from the multiple samples, where the second classifier can be used to determine a class to which a sample belongs based on the one or more features that characterize that sample;
   using the hardware to associate a second score variability with at least one of the one or more second scores using the feature variability;
   computing, with the hardware, a second probability of misclassification by the second classifier using one or more of the one or more second scores and the second score variability; and
   determining, with the hardware, a final probability of misclassification from a group of probabilities of misclassification that includes the first and second probabilities of misclassification.

15. A physical computer readable medium comprising machine-readable instructions for implementing the computer-implemented method of any of claims 1-7.

16. A physical computer readable medium comprising machine-readable instructions for implementing the computer-implemented method of claim 14.

* * * * *